United States Patent [19]
Dannenberg et al.

[11] Patent Number: 5,622,991
[45] Date of Patent: Apr. 22, 1997

[54] TREATING INFLAMMATORY LIVER DISORDERS BY ENTERALLY ADMINISTERING A FAT-CONTAINING DIET LOW IN POLYUNSATURATED FATS

[75] Inventors: Andrew J. Dannenberg, New York, N.Y.; Amin A. Nanji, Wellesley, Mass.

[73] Assignees: Cornell Research Foundation, Inc., Ithaca, N.Y.; New England Deaconess Hospital Corp., Boston, Mass.

[21] Appl. No.: 297,863

[22] Filed: Aug. 30, 1994

[51] Int. Cl.$^6$ ................................................ A01N 37/00
[52] U.S. Cl. .................................... 514/558; 514/560
[58] Field of Search ................................. 514/558, 560

[56] References Cited

U.S. PATENT DOCUMENTS

| | | | |
|---|---|---|---|
| 4,581,348 | 4/1986 | Schawartz et al. | 514/76 |
| 4,678,807 | 7/1987 | Cotter et al. | 514/552 |
| 4,703,062 | 10/1987 | Blackborn et al. | 514/552 |
| 4,810,726 | 3/1989 | Bistrian et al. | 514/552 |
| 5,112,827 | 5/1992 | Saunders et al. | 514/263 |

OTHER PUBLICATIONS

Chemical Abstracts 66: 44931 (1967).
91256374 Medline (1991).
CA 70: 55664 1968.
Dannenberg, A. J., et al, Biochemical Pharmacology, 44, 335–340, 1992.
Dannenberg, A. J., et al., J. Nutr. 122: 1607–1613, 1992.
The Merck Manual, 16th edition, 942–947, 1992.
Nanji, A. A., et al, Alcohol Clin. Exp. Res. 10, 271–273 (1986).
Nanji, A. A., et al, Proc. Soc. Exp. Biol. Med., 205, 243–246, 1993.
Tsukamoto, H., et al, Hepatology, vol. 12, No. 3, 599–608, 1990.
Dannenberg, A. J., et al, Biochimica et Biophysica Acta, 1210, 8–12 (1993).
Ekstrom, G., et al, Biochemical Pharmacology, 38, No. 8, 1313–1319 (1989).
Nanji, A. A., et al, Alcohol. Clin. Exp. Res. 13, No. 1, 15–19 (1989).
Nanji, A. A., et al, Life Sciences, vol. 44, pp. 223–227.
Tsukamoto, H., et al, Hepatology, vol. 6, No. 5, 814–822 (1986).
French, S. W., et al, Alcoholism: Clinical and Experimental Research, 13S–19S, 1986.
Nanji, A. A., et al, The Lancet, 681–683 (Mar. 1985).
Nanji, A. A., et al, American Journal of Pathology, vol. 142, No. 2, 367–373, Feb. 1993.
Naji, A. A., et al, J. Pharmacol. Exp. Ther., 266, No. 2, 1085–1090, 1993.
NutriHep Enteral Nutrition for Hepatic Patients (3 pages), Sep. 1993.

*Primary Examiner*—Paul J. Killos

[57] ABSTRACT

An enteral diet containing fat in an amount to provide from 20 to 50% of total calories, said fat containing less than 15% polyunsaturated fat (e.g., palm oil or medium chain triglycerides) is administered to mediate amelioration of the inflammation associated with the inflammatory liver, pancreatic and intestinal disorders, e.g., to promote healing of the liver in alcoholic hepatitis.

7 Claims, No Drawings

TREATING INFLAMMATORY LIVER DISORDERS BY ENTERALLY ADMINISTERING A FAT-CONTAINING DIET LOW IN POLYUNSATURATED FATS

This invention was made at least in part under National Institutes of Health grant number DK01992. The Government has certain rights in the invention.

TECHNICAL FIELD

This invention is directed at treating inflammation of the liver, pancreas and intestine. These include, for example, alcoholic hepatitis, viral hepatitis, pancreatitis, Crohn's disease and ulcerative colitis.

BACKGROUND OF THE INVENTION

Alcohol-related liver disease is a significant problem throughout the world. Cirrhosis is a leading cause of death in American urban men between the ages of 25-64. In addition, women appear to be even more susceptible than men to alcohol-related morbidity and mortality. Hospitalization costs, disability, and loss of productivity related to alcoholic liver disease amount to billions of dollars of costs annually in the United States.

Alcoholic hepatitis is the term for a clinicopathologic syndrome resulting from excessive alcohol consumption characterized by an acute or subacute clinical presentation and a distinctive appearance on liver biopsy. Mild cases may resolve spontaneously after cessation of alcohol consumption. Hospitalized patients with severe alcoholic hepatitis, however, have a one month mortality between 29-52%. In addition to the short-term mortality, the probability of alcohol-related hepatitis progressing to cirrhosis is estimated at 10-20%/yr. Long-term survival rates are influenced by continued alcohol consumption and nutritional factors, but return to normal liver function and architecture after an episode of alcoholic hepatitis are possible.

The high mortality rate for hospitalized alcoholic hepatitis patients is observed despite aggressive treatment of fluid and electrolyte disturbances, malnutrition, withdrawal symptoms, encephalopathy, gastrointestinal bleeding, and infection. Numerous trials for alcohol-related liver disease have been undertaken including treatment with anabolic steroids, colchicine, propylthiouracil, nutritional support, and insulin/glucagon. None of these treatments has been unequivocally associated with decreased mortality during the acute illness or diminished progression of alcoholic hepatitis to cirrhosis.

Nor is the scenario for other inflammatory liver, pancreatic and intestinal disorders much more positive.

There is no recognized treatment for chronic viral hepatitis other than interferon administration and interferon administration has proven effective only in a minority of patients and may cause significant side effects. Chronic vital hepatitis may progress to cirrhosis and/or liver cancer.

There is no known treatment for decreasing the inflammation in chronic pancreatitis.

The fact that no single approach is used for chronic Crohn's disease indicates the inadequacy of the various treatments.

Chronic ulcerative colitis can require proctocolectomy.

SUMMARY OF THE INVENTION

It is an object of the invention herein to employ enteral nutrition to reverse established injury in inflammatory liver, pancreatic and intestinal disorders including alcoholic hepatitis, viral hepatitis, chronic pancreatitis, Crohn's disease and ulcerative colitis, and particularly to administer an enteral fat-containing diet which is low in polyunsaturated fats and preferably which is high in saturated fats.

The present invention is directed to a method of treating a patient having an inflammatory liver, pancreatic or intestinal disorder including, e.g., alcoholic hepatitis, chronic viral hepatitis, chronic pancreatitis, chronic Crohn's disease and chronic ulcerative colitis, said method consisting essentially of administering an enteral diet containing fat in an amount so the fat provides from 20 to 50% of total calories, preferably from 30 to 40% of total calories, said fat containing less than 15% by weight polyunsaturated fat (total fatty acid source basis), preferably less than 10% by weight of polyunsaturated fat (total fatty acid source basis), preferably containing at least 45% by weight saturated fat (total fatty acid source basis), more preferably containing at least 50% by weight saturated fat (total fatty acid source basis).

DETAILED DESCRIPTION

As indicated by the term "enteral nutrition", administration herein is carried out enterally that is into the gastrointestinal tract by mouth (orally) or through a naso-gastric tube or by other modes.

The diet administered may be that normally associated with enteral nutrition for liver, pancreatic and intestinal disorders except that the fat component is modified to meet the percentages recited above. Thus the diet is preferably an enteral emulsion consisting essentially of from 25 to 75 grams per liter of source of said fat and preferably also contains from 100 to 400 grams per liter of carbohydrate, e.g., from dextrose, sucrose, lactose, maltodextrin, corn syrup, glucose oligosaccharides, hydrolyzed cereal solids, tapioca starch, modified cornstarch, hydrolyzed cornstarch, or pureed fruits and vegetables, from 15 to 75 grams per liter of amino acids and protein, e.g., from free L-amino acids including free essential amino acids, caseinates, hydrolyzed whey, hydrolyzed casein, hydrolyzed lactalbumin, meat protein and soy protein, and vitamins and minerals, e.g., Vitamin A, $B_1$, $B_2$, $B_3$, $B_5$, $B_6$, $B_{12}$, C, D, E, K, biotin, choline, folic acid, Ca, Cl, Cr, Cu, Fe, I, Mg, Mn, Mo, P, Se, and Zn. These emulsions contain, for example, 1 to 2 kcal/ml.

The enteral diet is administered, for example, to provide an average of 25 ml/hr. to 125 ml/hr. and an average of 500 to 3000 kcal/day.

We turn now to the fat constituent of the enteral diet which is a novel feature for the method herein. As indicated above, the enteral diet contains fat in an amount so the fat provides from 20 to 50% of total calories, preferably from 30 to 40% of total calories, said fat containing less than 15% by weight polyunsaturated fat (total fatty acid source basis), preferably less than 10% by weight of polyunsaturated fat (total fatty acid source basis), preferably containing at least 45% by weight saturated fat (total fatty acid source basis), more preferably containing at least 50% by weight saturated fat (total fatty acid source basis). The phrase "total fatty acid source basis" means that all the fatty acids in the diet are considered whether in the form of triglycerides, diglycerides, monoglycerides, free fatty acids, lecithin, or in other forms. The invention herein contemplates and includes use of compositions where saturated fatty acids constitute all the fatty acids on a total fatty acid source basis. Suitable fats which maybe used as the sole fat constituent to meet the requirement herein of no more than 15% by weight of polyunsaturated fat (total fatty acid source basis) include butter fat, cocoa butter, coconut oil, lard, medium chain triglycerides (i.e., triglycerides which mainly contain $C_8$ and $C_{10}$ fatty acids, i.e., caprylic acid and capric acid), palm oil, palm kernal oil and tallow. These may be used in admixture with fats or other sources of fatty acids which alone do not meet said requirement when the admixture meets said requirement. Suitable fats also include those which are hydrogenated to meet said requirement.

The invention is illustrated in the following examples.

In the examples, an intragastric feeding rat model for alcoholic injury is used. This rat model is described in Tsukamoto, H., et al, Hapatology, 6, No. 5, 814–822 (1986); in French, S. W., et al, Alcohol Clin. Exp. Res. 10:13S–19S (1986); and in Tsukamoto, H., et al, Hepatology, 12, 599–608 (1990). In accordance with this rat model, rats are fed a diet containing menhaden fish oil and ethanol for 6 weeks to induce alcohol-related liver injury. The amount of ethanol was initially 8 g/kg/day and was increased up to 16 g/kg/day as tolerance developed. The amount of menhaden fish oil was maintained at 35% of total calories. The diet also included protein (at about 25% of calories) and dextrose which together with the ethanol gave the remainder of the calories. Vitamins and minerals were also given as described in French et al and in Tsukamoto et al. In comparison to humans, the rats at the end of the 6-week period represent the equivalent of patients admitted to the hospital with alcohol related liver disease whereupon alcohol consumption ceases and nutritional support begins.

In Examples I and II, the protein consisted of casein hydrolysate.

EXAMPLE I

Fifteen male Wistar rats (225–250 g) were fed ethanol and menhaden fish oil for a six-week period in accordance with the intragastric feeding rat model for alcoholic injury described above. These were divided into three groups, each containing 5 of the rats.

At the end of the six-week period, a control group of 5 of the rats was sacrificed and determinations were made as described below.

At the end of the six-week period, biopsies were carried out on the second and third groups of 5 rats each, to confirm the occurrence of liver injury.

At the end of the six-week period, the second group of 5 rats was switched to a diet of menhaden fish oil (35% of total calories), protein (about 25% of total calories) and dextrose (remainder of total calories) for two weeks with vitamins and minerals continued as before. The menhaden fish oil was found by analysis to contain the following percentages of fatty acids (total fatty acid basis): 0.2% C12:0, 10.3% C14:0, 1.1% C15:0, 20.0% C16:0, 1.2% C17:0, 3.4% C18:0, 2.1% C20:0, 14.8% C16:1, 0.3% C17:1, 12.3% C18:1, 2.6% C20:1, 0.6% C22:1, 0.2% C24:1, 1.6% C16:2, 2.0% C18:2, 3.7% C18:3, 0.5% C20:2, 0.4% C20:3, 0.7% C20:4, 9.8% C20:5, 1.8% C22:5, 6.1% C22:6 and 1.6% unknown and C19:1 alcohol, providing totals of 38.3% saturated fatty acid and 26.6% polyunsaturated fatty acid. At the end of the two-week period, the five rats of this group were sacrificed and determinations were made as described below.

At the end of the six-week period, the third group of 5 rats was switched to a diet of palm oil (35% of total calories), protein (about 25% of total calories) and dextrose (the remainder of total calories) for two weeks, with vitamins and minerals continued as before. The palm oil was found by analysis to contain the following percentages of fatty acids (total fatty acid basis): 0.4% C12:0, 1.2% C14:0, 44.8% C16:0, 3.9% C18:0, 50.0% C18:1n–9, 8.4% C18:2n–6 and 0.3% C20:0, providing totals of 50.6% saturated fatty acid and 8.4% polyunsaturated fatty acid. At the end of the two-week period, the five rats of this group were sacrificed and determinations were made as described below.

Upon sacrifice, the livers of each group of rats were sectioned, formalin-fixed, hematoxylin and eosin stained for light microscopy and evaluated for inflammatory cells per $mm^2$, foci of necrosis per $mm^2$, and degree of fatty liver (scale of 1–4). In addition, evaluation for conjugated dienes was carried out by obtaining lipid extract of liver homogenate and measuring the optical density at 232 nm according to the method described in Recknagel, R. O., et al, Meth. Enzymol, 105:331–337 (1984).

For the control group, the following results were obtained: Fatty liver, 4.0±0.0; necrosis, 1.2±0.5 foci/$mm^2$; inflammation, 27.3±7.1 cells/$mm^2$; conjugated dienes, 0.59±0.30.

For the second group of rats, the following results were obtained: Fatty liver, 2.8±0.8; necrosis, 0.8±0.6 foci/$mm^2$; inflammation, 17.3±7.8 cells/$mm^2$; conjugated dienes, 0.33±0.6.

For the third group of rats, the following results were obtained: Fatty liver, 0.8±0.7; necrosis, 0.2±0.1 foci/$mm^2$; inflammation, 2.0±1.0 cells/$mm^2$; conjugated dienes, 0.14±0.01.

The results for the group of rats fed palm oil were significantly better ($p<0.01$) than the results for the other groups.

A comparison of liver fatty acid composition in the groups for rats fed palm oil/protein/dextrose versus menhaden fish oil/dextrose showed significantly higher levels of 18:2 n–6 (10.8±0.7 vs. 4.2±0.5) and 18:1 n–9 (15.9±0.8 vs. 9.7±1.2) and significantly lower levels of 20:5 n–3 (8.8±1.8 vs. 14.2±1.3) and 22:6 n–3 (10.8±2.9 vs. 15.2±0.4) in rats fed palm oil/protein/dextrose.

Liver levels of alpha and gamma tocopherols were similar in all groups.

The results show that feeding palm oil to rats having established alcoholic liver disease caused a significant reduction in degree of fatty liver, necrosis and inflammation whereas feeding menhaden fish oil to rats having established alcoholic liver disease led to minimal improvement in liver pathology.

EXAMPLE II

An experiment similar to that of Example I was carried out with 10 rats where at the end of the six week period 5 rats constituted the control group and 5 rats were switched to medium chain triglycerides (35% of total calories), protein (about 25% of total calories) and dextrose (remainder of total calories) with vitamins and minerals continued as before for 2 weeks. The medium chain triglycerides contained only saturated fatty acids.

The results for the control group were similar to those for the control group of Example I.

For the group of rats fed medium chain triglycerides and dextrose, the following results were obtained: Fatty liver, 1.0±0.6; necrosis, 0.2±0.2 Foci/$mm^2$; inflammation, 1.9±1.6 cells/$mm^2$.

The results show that feeding medium chain triglycerides to rats having established alcoholic liver disease led to significant reduction in degree of fatty liver, necrosis and inflammation.

Palm oil (used in Example I) normally contains some Vitamin E. Medium chain triglycerides do not contain Vitamin E. This example shows that the same results as are obtained in Example I are obtained without Vitamin E being present.

EXAMPLE III

A patient with alcoholic hepatitis is admitted to a hospital. Liver biopsy shows fatty liver of about 4.0±0.0, necrosis of about 15.8±1.9 foci/mm$^2$ and inflammation of about 100.2±10.9 cells/mm$^2$.

Diet is administered orally consisting of enteral emulsion containing 45 g/L L-amino acids, 170 g/L maltodextrin/sucrose and 35 g/L palm oil or medium chain triglycerides at the rate of 600 ml/day.

At the end of 6 weeks, liver biopsy shows significantly improved liver pathologies.

Variations in the invention will be obvious to those skilled in the art. Thus, the invention is defined by the claims.

What is claimed is:

1. A method of treating a patient having an inflammatory liver disorder selected from the group consisting of alcoholic hepatitis and viral hepatitis, said method consisting essentially of administering to said patient an enteral diet containing fat in an amount so the fat provides from 20 to 50% of total calories, said fat containing more than 45% saturated fatty acids on a total fatty acid source basis and less than 15% polyunsaturated fatty acids on a total fatty acid source basis, thereby to mediate amelioration of the inflammation associated with said disorder.

2. The method of claim 1 wherein the inflammatory disorder is alcoholic hepatitis and the treatment mediates healing of the liver.

3. The method of claim 1 wherein the method consists essentially of administering to said patient an enteral diet containing fat so the fat provides from 30 to 40% of total calories, said fat containing less than 10% polyunsaturated fatty acids on a total fatty acid source basis and more than 50% saturated fatty acids on a total fatty acid source basis.

4. The method of claim 3 wherein the fat consists of palm oil.

5. The method of claim 3 wherein the fat consists of medium chain triglycerides.

6. The method of claim 1 wherein said disorder is ethanol related.

7. The method of claim 1 wherein said disorder is chronic viral hepatitis.

* * * * *